(12) United States Patent
Jones et al.

(10) Patent No.: US 6,495,370 B1
(45) Date of Patent: Dec. 17, 2002

(54) INHIBITION OF GLUTATHIONE TRANSFERASE BY HALOENOL LACTONES

(75) Inventors: A. Daniel Jones, Sacramento; Alyson E. Mitchell, Davis; Bruce D. Hammock, Davis; Jiang Zheng, Davis, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/639,392

(22) Filed: Aug. 15, 2000

Related U.S. Application Data

(62) Division of application No. 09/094,926, filed on Jun. 15, 1998, now Pat. No. 6,103,665, which is a division of application No. 08/426,593, filed on Apr. 21, 1995, now Pat. No. 5,767,147.

(51) Int. Cl.[7] .......................... G01N 33/00; C12Q 1/48
(52) U.S. Cl. ........................................ 436/127; 435/15
(58) Field of Search ................................ 514/473, 459, 514/460, 471; 436/127; 435/15

(56) References Cited

PUBLICATIONS

Beckett, et al., *Advances in Clin. Chem.*, 30:281–380(1993).
Caccuri, et al., *Biochem. and Mol. Biol. International*, 32(5):819–29 (1994).
Chakravarty, et al., *J. Biol. Chem.*, 257(2):610–2 (1982).
Clark, The Glutathione S–Transferases and Resistance to Insecticides Victoria University of Wellington, Wellington, NZ 369–379.
Daniels, et al., *Biochemistry*, 25(6):1436–44 (1986).
Daniels, et al., *J. Biol. Chem.*, 258(24):15046–53 (1983).
Dauterman, The role of Glutathione S–Transferases in Herbicide Tolerance and Resistance N.C. State University, Department of Toxicology, Raleigh, NC 347–355.
Eriksson, et al., Liver Nodules and Drug Resistance Department of Pathology, Huddinge Hospital, Sweden 329–340.
Hazen, et al., *J. Biol. Chem.*, 266(11):7227–32 (1991).
McLellan, et al., Differential Regulation of Murine Glutathione S–Transferases by Xenobiotics University Department of Clinical Chemistry, The Royal Infirmary, Edinburgh, Scotland.
Moscow, et al., Glutathione S–Transferase PI and Antineoplastic Drug Resistance Medicine Branch, National Cancer Institute, Bethesda, MD 319–327.
Naruto, et al.,*J. Am. Chem. Soc.*, 107(18):5262–5270 (1985).
Pandiella, et al., *J. Biol. Chem.*, 267(33):24028–33 (1992).
Rai, et al., *J. Med. Chem.*, 35(22):4150–9 (1992).
Ramanadham, et al., *Biochemistry*, 32(1):337–46 (1993).
Ramanadham, et al., *Biochemistry*, 32(20):5339–51 (1993).
Sofia, et al., *J. Med. Chem.*, 29(2):230–8 (1986).
Tew, et al., Glutathione S–Transferases and Resistance to Alkylating Agents Department of Pharmacology, Fox Chase Cancer Center, Philadelphia, PA 309–317.
Tu, et al., Molecular Basis of Glutathione S–Transferase-–mediated Atrazine Tolerance in Z. MAYS L. Department of Molecular and Cell Biology, The Pennsylvania State University, University Park, PA 357–367.
Wolf, et al., Glutathione S–Transferases in Resistance to Chemotherapeutic Drugs Imperial Cancer Research Fund, Laboratory of Molecular Pharmacology, Department of Biochemistry, Edinburgh, Scotland 295–306.
Zupan, et al., *J. Med. Chem.*, 36(1):95–100 (1993).

*Primary Examiner*—Amelia Owens
(74) *Attorney, Agent, or Firm*—Townsend and Townsend and Crew LLP

(57) ABSTRACT

This invention relates to novel haloenol lactone compounds. These compounds have the following general structure:

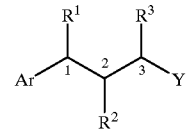

in which Ar is an aryl group and Y is a haloenol lactone moiety.

The compounds of the invention are useful for the specific measurement of particular isoenzymes of glutathione S-transferase. Measurement of glutathione S-transferase isoenzymes has importance in diagnostic medicine. The compounds of the invention are also useful for treatment of drug resistance in cancer and for preventing herbicide resistance in plants.

6 Claims, 10 Drawing Sheets

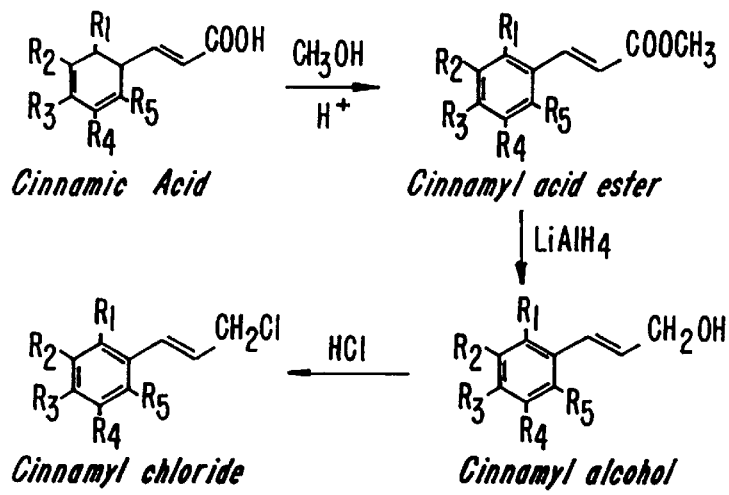

COMMERCIALLY AVAILABLE CINNAMIC ACIDS (ALDRICH CHEMICAL CO.):

| | | |
|---|---|---|
| 1. $R_1$ = OH | 11. $R_3$ = F | 21. $R_3$ = $CH_3$ |
| 2. $R_2$ = OH | 12. $R_1$ = $CF_3$ | 22. $R_2$ = OH, $R_3$ = $OCH_3$ |
| 3. $R_3$ = OH | 13. $R_2$ = $CF_3$ | 23. $R_2$ = $OCH_3$, $R_3$ = OH |
| 4. $R_1$ = Cl | 14. $R_3$ = $CF_3$ | 24. $R_2$ = OH, $R_3$ = OH |
| 5. $R_2$ = Cl | 15. $R_1$ = $NO_2$ | 25. $R_1$ = $OCH_3$, $R_2$ = $OCH_3$ |
| 6. $R_3$ = Cl | 16. $R_2$ = $NO_2$ | 26. $R_1$ = $OCH_3$, $R_3$ = $OCH_3$ |
| 7. $R_2$ = Br | 17. $R_3$ = $NO_2$ | 27. $R_1$ = $OCH_3$, $R_4$ = $OCH_3$ |
| 8. $R_3$ = Br | 18. $R_1$ = $OCH_3$ | 28. $R_2$ = $OCH_3$, $R_3$ = $OCH_3$ |
| 9. $R_1$ = F | 19. $R_2$ = $OCH_3$ | 29. $R_2$ = $OCH_3$, $R_4$ = $OCH_3$ |
| 10. $R_2$ = F | 20. $R_3$ = $OCH_3$ | 30. $R_2$ = $OCH_3$, $R_3$ = OH, $R_4$ = $OCH_3$ |

CINNAMYL CHLORIDES CAN ALSO BE PREPARED FROM VARIOUS AROMATIC ALDEHYDES:

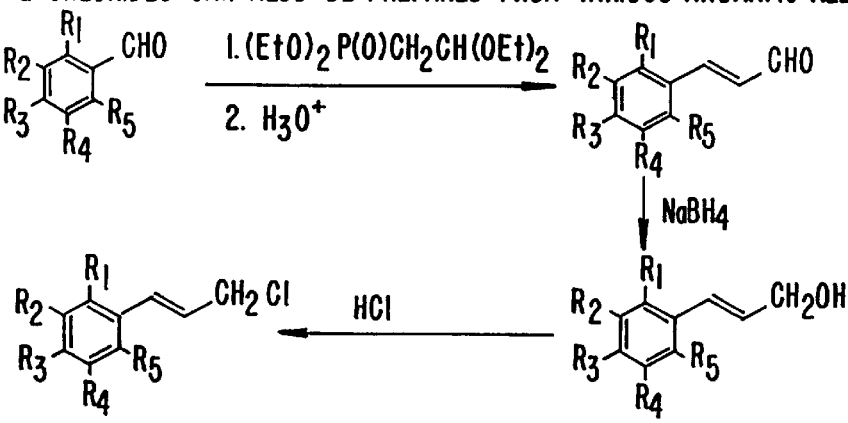

FIG. 2.

ADDUCT 3

INHIBITION OF GLUTATHIONE TRANSFERASE BY HALOENOL LACTONES

This application is a Division of Ser. No. 09/094,926 filed Jun. 15, 1998 now U.S. Pat. No. 6,103,665 which is a Division of Ser. No. 08/426,593 filed Apr. 21, 1995 now U.S. Pat. No. 5,767,147.

This invention was made with government support under Grant No. ES04699 awarded by the National Institutes of Health. The Government has certain rights in this invention.

FIELD OF THE INVENTION

This invention relates to novel haloenol lactone compounds. These compounds are useful for the specific measurement of particular isoenzymes of glutathione S-transferase. The measurement of glutathione S-transferase isoenzymes has importance in diagnostic medicine. The compounds of the invention are also useful for treatment of drug resistance in cancer and for preventing herbicide resistance in plants.

BACKGROUND OF THE INVENTION

Glutathione S-transferase enzymes (GST enzymes) are a superfamily of enzymes that play an important role in the metabolism of a variety of organic compounds, including chemotherapeutic drugs, carcinogens, environmental pollutants and other harmful foreign compounds. GST enzymes have been reported to be present in a wide variety of species including bacteria, yeast, plants, nematodes, insects, birds, fish and mammals.

GST enzymes catalyze the conjugation of glutathione to a variety of different organic compounds. The glutathione thiolate anion serves as a nucleophile in the enzyme catalyzed reaction to attack electrophilic carbon, nitrogen, sulfur or oxygen atoms of a substrate molecule. See Beckett, et al. (1993) *Adv. Clin. Chem.* 30:281–380 for a detailed description of specific GST-catalyzed reactions.

There are a large number of GST isoenzymes in all mammalian species. These isoenzymes are encoded by four different families of GST genes, which have been designated alpha, mu, pi and theta. The GST isoenzymes from all four families are cytosolic enzymes and are dimers with a submit molecular weight of about 26 kDa. There are multiple isoenzyme forms in both the alpha and mu GST families, and these enzymes are located primarily in the liver. The pi family of GST isoenzymes are found in the liver as well as in a large number of other tissues. Thus far, only one or two isoenzymes in the pi family have been identified. The theta family of GST enzymes has only recently been isolated from liver and it is unknown how many isoenzymes exist in this family. In addition, a microsomal GST enzyme has recently been identified that is apparently structurally unrelated to the above described cytosolic enzymes. See Beckett, et al., supra for a more detailed description of GST isoenzymes.

Many cancers treated with chemotherapeutic drugs develop resistance to the particular chemotherapeutic drugs used in treatment. Furthermore, overexpression of GST enzymes is an important cellular mechanism involved in the development of drug resistance by tumor cells. Isoenzymes from both the alpha and pi GST families play a role in the development of resistance to chemotherapeutic drugs. For example, overexpression of alpha GST isoenzymes has been implicated in drug resistance to alkylating agents such as chlorambucil and cyclophosphamide. In addition, the pi GST isoenzymes have been shown to be involved in the development of drug resistance to a variety of other chemotherapeutic agents such as adriamycin, vinblastine, actinomycin D and colchicine.

Herbicide resistance in weeds has emerged as a significant problem in agriculture. Furthermore, overexpression of GST enzymes in plant cells is an important mechanism for development of herbicide resistance. In particular, overexpression of GST enzymes appears to be involved in the development of resistance to chloracetanalides, thiocarbamates, and to triazines such as atrazine.

As described above, GST isoenzymes have medical importance due to their role in mediating drug resistance in cancer patients. In addition, the measurement of GST isoenzymes in vitro also has importance in diagnostic medicine. For example, the measurement of the pi isoenzyme of GST in tissue specimens is useful in pathology for the detection and diagnosis of a variety of different tumors. In addition, measurement of the alpha form of GST in blood is useful for the detection and monitoring of a variety of different forms of liver disease. (See Beckett, et al., supra for a detailed description of the clinical applications of GST isoenzyme measurements.

There is a need for selective inhibitors of GST isoenzymes for treatment of drug resistance in cancer patients. There is also a need for GST isoenzyme inhibitors to be used with herbicides to prevent herbicide resistance in plants. In addition, there is a need for selective inhibitors of GST isoenzymes to be used in the in vitro diagnostic testing for the measurement of specific forms of GST isoenzymes. These and other needs are addressed by the present invention.

SUMMARY OF THE INVENTION

The invention provides for novel haloenol lactone compounds. The invention also provides for pharmaceutical compositions containing a pharmaceutically acceptable carrier and an amount of a haloenol compound of the invention that is effective in inhibiting a GST enzyme in an animal. For example, the animal can be a mammal.

The invention also provides for methods of inhibiting a GST enzyme in an animal. These methods involve the administration of a pharmaceutically acceptable carrier and an amount of a haloenol compound of the invention which is effective for inhibiting a GST enzyme in the animal. The animal can be, for example, a mammal.

In addition, the invention provides for methods of inhibiting a GST enzyme in a plant cell by contacting the plant cell with an amount of a haloenol lactone of the invention that is effective for inhibiting the GST in the plant cell. The haloenol lactone can be applied to the plant cell along with an herbicide. The herbicide can be, for example, a triazine, a chloroacetanalide, or a thiocarbamate herbicide.

The invention also provides for methods of detecting a GST isoenzyme in a biological specimen. These methods involve the measurement of GST enzyme activity in the presence and absence of an amount of a haloenol lactone of the invention that is effective to inhibit a GST isoenzyme. The GST isoenzyme can be, for example, GST pi or GST alpha isoenzyme.

BRIEF DESCRIPTION OF THE DRAWINGS

FIG. 2: (top) Reaction scheme for synthesis of substituted cinnamyl chloride reagents. (middle) Examples of commercial sources of substituted cinnamic acids. (bottom) Alternate synthesis pathway for substituted sinnamyl chloride reagents.

DESCRIPTION OF THE PREFERRED EMBODIMENT

A. Definitions

Figure 1:
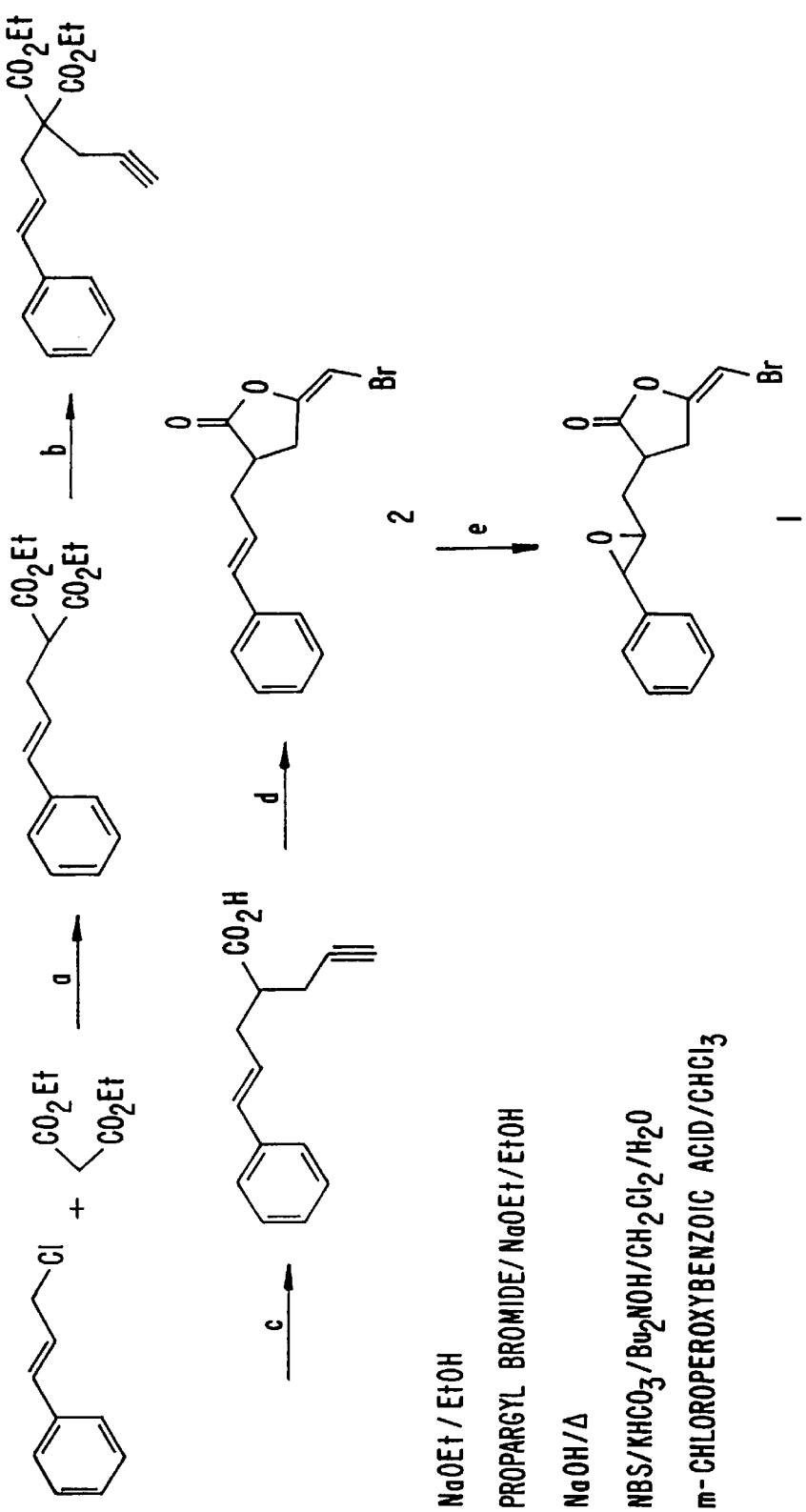
FIG. 1: Reaction scheme for synthesis of methylidenetetrahydro-2-furanone derivatives 1 and 2.

As used herein, the term "alkyl" refers to a saturated hydrocarbon radical which can be straight chain or branched chain. Preferably, for the present invention, alkyl groups contain 1–10 carbon atoms and more preferably 1–5 carbon atoms. All numerical ranges in this specification are intended to be inclusive of their upper and lower limit. The term "straight chain alkyl" refers to an unbranched alkyl group as defined above. The term "branched chain alkyl" refers to a branched alkyl group as defined above. For example, the term "$C_1$–$C_5$" alkyl group as used herein refers to both straight chain alkyl groups and branched chain alkyl groups that contain from 1 to 5 carbon atoms. Similar nomenclature is used to specify more specific alkyl structures. For example, the term "$C_3$–$C_5$ branched chain alkyl group" refers to branched chain alkyls of 3–5 carbon atoms.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aryl" refers to an aromatic substituent which may be a single ring or multiple rings which are fused together or linked covalently. The aromatic rings may each contain heteroatoms, for example, phenyl, naphthyl, biphenyl, thienyl, pyridyl and quinoxalyl. The aryl moieties may also be optionally substituted with halogen atoms, or other groups such as nitro, carboxyl, alkoxy, alkyl groups, $CF_3$, CN, alkylthio groups, methyl sulfonyl groups, and the like. Additionally, the aryl radicals may be attached to other moieties at any position on the aryl radical which would otherwise be occupied by a hydrogen atom (such as, for example, 2-pyridyl, 3-pyridyl and 4-pyridyl).

The term "lactone" is well known to those of skill in the art and refers to cyclic ester of a carboxylic acid group that is typically formed by intramolecular reaction of hydroxylated or halogenated carboxylic acids with the elimination of water. Lactones are thus cyclic ring structures containing a ester linkage. Haloenol lactones are typically 4–8 membered lactone rings, preferably 5–6 membered lactone rings. The term "haloenol lactone" as used herein refers to a lactone in which there is a double bond between the carbon atom attached to the ring oxygen (not the carbonyl carbon) and an adjacent carbon atom. This adjacent carbon atom can be a ring member or can be exocyclic. A halogen or a halogen-substituted alkyl group is attached to this adjacent carbons atom. (See Formulas III and IV herein for examples of haloenol lactones in which the double bond and the adjacent carbon atom are external to the cyclic lactone ring. See Formulas V herein for an example a of haloenol lactone in which the double bond and the adjacent carbon atom are members of the cyclic ring.)

The term "biological specimen" as used herein refers to any specimen obtained from a living organism or an organism that has died. Examples of biological specimens include body fluids and tissue samples. Biological specimens also include entire living organisms including plants, microorganisms, insects, parasites and mammals.

B. Introduction

The novel haloenol lactones of the invention are enzyme inhibitors. Preferably the compounds of the invention are inhibitors of GST isoenzymes. As is described above, there are a large number of GST isoenzymes in mammals. These isoenzymes are encoded by four different families of genes for the cytosolic GST enzymes, plus-at least one additional gene for a microsomal GST enzyme. The haloenol lactone compounds of the invention can be inhibitors of all GST isoenzymes. Alternatively and preferentially, the compounds of the invention are selective inhibitors or specific inhibitors of one or more GST isoenzymes. The terms "selective inhibitors of GST isoenzymes" or "specific inhibitors of GST isoenzymes" as used herein, refer to compounds are capable of selectively inhibiting one or more isoenzymes of GST. Selective inhibition means that a compound has a greater inhibitory effect on one isoenzyme of GST than it does on another GST isoenzyme. It is possible that a selective inhibitor of a GST isoenzyme may inhibit all GST isoenzymes to some extent, but that one or more GST isoenzymes may be inhibited to a lesser extent than the others. For instance, the compounds of the invention can be selective inhibitors of the GST pi isoenzyme. Compounds 1 and 2 as described herein are selective inhibitors of GST pi isoenzymes. (See Example 3, herein)

The haloenol compounds of the invention can inhibit GST by a variety of mechanisms. Preferentially, the compounds of the invention are site-directed enzyme inhibitors that react with the active site region of GST. More preferentially, the compounds of the invention are irreversible, mechanism-based inhibitors of GST enzymes. Mechanism-based enzyme inactivators are often considered to be the most promising specific site-directed enzyme inhibitors. Their specificity resides within the catalytic mechanism of the enzyme itself. Mechanism-based inactivators can be transformed into potent electrophiles through the normal catalytic reaction of the enzyme (see Walsh, C. (1982) *Tetrahedron*, 38: 871–909).

The haloenol lactone compounds of the invention are useful for treatment of drug resistance that is associated with overexpression of GST isoenzymes. The compounds of the invention are useful for treatment of drug resistance due to a variety of different chemotherapeutic drugs, including, for example, alkylating agents such as chlorambucil and cyclophosphamide and other chemotherapeutic agents such as adriamycin, vinblastine, actinomycin D and colchicine.

The haloenol compounds of the invention have other medical uses in addition to the treatment of drug resistance. For example, the compounds of the invention are also useful in the treatment of a variety of parasitic infections. GST enzymes are an attractive target for attacking a variety of parasites because the enzyme plays an essential role in the detoxification system in many parasites. Examples of parasitic infections that can be treated by the compounds of the invention include schistosomiasis and other helminthic diseases, human filarial parasites and liver and blood flukes.

The haloenol compounds of the invention also have uses in diagnostic medicine. In particular, the compounds of the invention are useful for the measurement of particular isoenzymes of GST in biological specimens. The haloenol compounds of the invention can be selective inhibitors of particular forms of GST isoenzymes. This property of selective inhibition can be used in GST enzyme assays to measure particular GST isoenzymes. For example, measurement of the pi isoenzyme of GST in tissue specimens is useful in pathology for the detection and diagnosis of a variety of different tumors. In addition, measurement of the alpha form of GST in blood is useful for the detection and monitoring of a variety of different forms of liver disease.

In addition to the medical uses, the haloenol lactone compounds of the invention are useful in agriculture. In particular, the compounds of the invention are useful for treating herbicide resistance related to overexpression of GST isoenzymes. For example, resistance to chloracetanalides, thiocarbamates, and to triazines such as atrizine can be treated by the compounds of the invention.

C. The Haloenol Lactone Compounds of the Invention

The haloenol compounds of the invention include those compounds having the following formula:

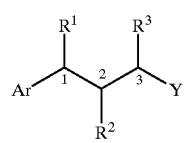

Formula I in which:
Ar is an aryl group;
$R^1$ and $R^2$:
a) together form a double bond between carbon atoms 1 and 2;
b) together form an epoxy group between carbon atoms 1 and 2: or
c) are the same or different and are independently selected from the group consisting of H, OH, glutathione thioether, glutathione-S-oxide thioether, and glutathione-S,S-dioxide thioether;

$R^3$ is selected from the group consisting of H, OH, glutathione thioether, glutathione-S-oxide thioether, and glutathione-S,S-dioxide thioether; and Y is a haloenol lactone.

The aryl group of Formula I can be a radical of the formula:

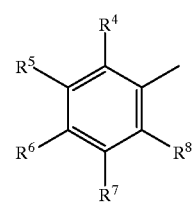

Formula II in which:

$R^4$, $R^5$, $R^6$, $R^7$, and $R^8$ are the same or different and are independently selected from the group consisting of H, a $C_1$–$C_5$ alkyl group, a $C_1$–$C_5$ alkoxy group, a halogen, $NO_2$, $CF_3$, CN, a $C_1$–$C_5$ alkylthio group, and a methyl sulfonyl group.

The aryl group of formula I can also be, for example, a naphthyl group. The naphthyl group or any of the other aryl groups of formula I can also be optionally substituted with one or more members selected from the group consisting of H, a $C_1$–$C_5$ alkyl group, a $C_1$–$C_5$ alkoxy group, a halogen, $NO_2$, $CF_3$, CN, a $C_1$–$C_5$ alkylthio group, and a methyl sulfonyl group.

The $C_1$–$C_5$ alkyl groups can be either straight chain or branched chain alkyl groups. Examples of such groups include methyl and tert-butyl moieties. In the phenyl ring structure of Formula II, the H, $C_1$–$C_5$ alkyl group, $C_1$–$C_5$ alkoxy group, halogen, $NO_2$, $CF_3$, CN, the $C_1$–$C_5$ alkylthio group, and the methyl sulfonyl group moieties are preferentially attached to positions $R^5$, $R^6$ or $R^7$. Also preferentially, $R^2$ and $R^3$ in formula I are H or OH and the glutathione thioether, glutathione-S-oxide thioether or the glutathione-S,S-dioxide thioether moiety is attached to $R^1$.

The haloenol lactone moiety of formula I can be any haloenol lactone moiety. For example, the haloenol lactone can be one of the three haloenol structures shown in formulas III–V, below:

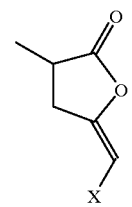

Formula III

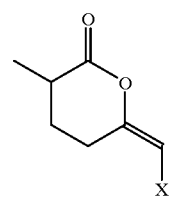

Formula IV

Formula V

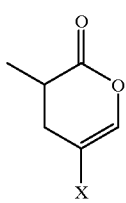

wherein X is a halogen. A $C_1-C_3$ alkyl group can also be attached to the carbon atom to which the halogen is attached.

Compounds 1 and 2, as described herein, are particular species of the claimed haloenol lactones in which Ar is the radical of Formula I and Y is the radical of Formula III. For compound 1, $R^4-R^8$ are H; $R^1$ and $R^2$ together form an epoxy group between carbon atoms 1 and 2; and $R^3$ is H. For compound 2, $R^4-R^8$ are H; $R^1$ and $R^2$ together form a double bond between carbon atoms 1 and 2; and $R^3$ is H.

D. Synthesis of the Haloenol Lactone Compounds

The haloenol lactone compounds of the invention can be synthesized by modifications of the reaction scheme shown in FIG. 1. The synthesis of haloenol lactones having an aryl group which is a phenyl radical is demonstrated in Example 1 and shown in FIG. 1.

Cinnamyl chloride derivatives substituted with, for example, $C_1-C_5$ alkyl groups, $C_1-C_5$ alkoxy groups, halogens, $NO_2$, $CF_3$, CN, $C_1-C_5$ alkylthio groups, and methyl sulfonyl groups can be prepared from substituted cinnamic acid derivatives which are commercially available or which can be prepared by methods known to those of skill in the art.

Cinnamyl chloride derivatives are key intermediates used in the total synthesis of haloenol lactone inhibitors of GST. Numerous substituted cinnamic acid derivatives are available from commercial sources. Examples of substituted cinnamic acids which are available commercially from Aldrich Chemical Company, Milwaukee, Wis., U.S.A., are shown in FIG. 2. When substituents are not available, the nitro-substituted cinnamic acids can be converted to the desired product via the process of reducing the nitro group to an amino group, diazotizing the amino group, and displacing the diazonium group using any one of a variety of nucleophilic substances known to those practiced in the art of organic synthesis. For instance, such an approach can be used to synthesize the methylthio- and methyl sulfonyl-substituted cinnamic acids which are precursors for methylthio- and methyl sulfonyl-substituted haloenol lactones. As a specific example of this reaction, 4-Nitrocinnamic acid is reacted with $SnCl_2$ to produce 4-aminocinnamic acid, which is treated with $NaNO_2$/HCl to produce a Diazonium chloride derivative of cinnamic acid. This derivative can be reacted with a nucleophile to produce the desired substituted cinnamic acid.

Methylthio groups can be introduced to aromatic rings using the above-described reactions (*J. Org. Chem.* 55:2736–2742, 1990), employing potassium ethylxanthate as nucleophile. For example, the methylthio group can be oxidized to the methyl sulfonyl group using $NaIO_4$ or $KMnO_4$ (B. S. Furniss, A. J. Hannaford, P. W. G. Smith and A. R. Tatchell, *Vogel's Textbook of Practical Organic Chemistry*, 5th Edition, Wiley, N.Y., 1989, P. 792). Other alkyl groups can be introduced to aromatic rings using Friedel-Crafts alkylation chemistry (R. C. Larock, *Comprehensive Organic Transformations*, VCH Publishers, 1989, pp. 69–70). Alkyl ether substitutents can be introduced by alkylation of the hydroxy-substituted cinnamic acids using alkyl halides and a base such as sodium hydroxide (R. C. Larock, *Comprehensive Organic Transformations*, VCH Publishers, 1989, pp. 445–453).

Further conversion of substituted cinnamic acids to the cinnamyl chlorides can be accomplished using the common chemical transformations of methyl esterification (e.g., via reaction with methanol under conditions of acidic catalysis) followed by reduction of the ester group to an alcohol with $LiAlH_4$. Reaction of the resulting cinnamyl alcohol with hydrochloric acid gives the desired cinnamyl chloride intermediates (see FIG. 2), and these can be used in turn to synthesize the various haloenol lactones. All of the reactions used in these transformations are commonly known to those of skill in synthetic organic chemistry.

Synthesis of haloenol lactone compounds of the invention having aryl groups other than phenyl can be performed by substituting other starting reagents for the cinnamyl chloride reagent. For example, naphthyl derivatives would be prepared from naphthaldehyde via naphthyl analogues of the cinnamyl halides. Substitutions such as $C_1-C_5$ alkyl groups, $C_1-C_5$ alkoxy groups, halogens, $NO_2$, $CF_3$, CN, $C_1-C_5$ alkylthio groups, and methyl sulfonyl can be introduced onto the aryl groups by using appropriate starting materials that are commercially available or which are synthesized by methods known to those of skill in the art, as described above.

In general, synthesis of the haloenol lactone cyclic ring radical can be performed by haloenolactonization of a pentynoic acid derivative. (See FIG. 1 and Kraft (1981) *J. Am. Chem. Soc.* 103:5459–5466. See Example 1 and FIG. 1, herein, for an example of the synthesis of the haloenol lactone of Formula III, herein. Other haloenol lactone moieties can be synthesized by modifications of this reaction scheme. For example, the haloenol lactone of formula IV, which contains an exocyclic bromoethylene group, can be synthesized by substituting 4-bromo-butyne for the propargyl bromide reagent shown in FIG. 1. Haloenol lactones illustrated by the structure Formula V can be synthesized by the following method: 1,3-Cyclopentanedione can be converted to 3-bromo-cyclopenten-1-one by reaction with $PBr_5$ following reactions used by G. A. Krafft and J. A. Katzenellenbogen, *J. Am. Chem. Soc.* 103:5459–5466, (1981). This reaction product can be incubated with cinnamyl chloride in the presence of potassium tert-butoxide to form 5-cinnamyl-3-bromocyclopenten-1-one. Baeyer-Villiger oxidation of this intermediate using trifluoroperoxyacetic acid yields the desired haloenol lactone 5-bromo 3-cinnamyl-2(4H)-pyranone (Formula V).

The glutathione substitions on carbons 1–3 shown in formula I can be prepared by reaction of a limiting amount of glutathione with the haloenol lactone compounds of the invention. For example, 3-cinnamyl-($\alpha$-S-glutathionyl,$\beta$-hydroxy)-5(E)-bromomethylidenetetrahydro-2-furanone can be achieved through reaction of a limiting amount of glutathione with compound 1.

E. Testing of the Haloenol Lactone Compounds

The haloenol lactone compounds synthesized as described above are tested for their ability to inhibit GST isoenzymes. GST isoenzymes can be purified or partially purified from a variety of species including plants and mammals by methods known to those of skill in the art. For example, GST alpha, mu and pi isoenzymes can be purified from mouse liver as described in Example 2, herein.

The haloenol lactone compounds are incubated with purified or partially purified GST isoenzymes as described above and GST enzyme activity is determined by standard enzyme assay procedures. Enzyme inhibition testing protocols and GST assay procedures are well known to those of skill in the art. For instance, testing for selective inhibition of particular GST isoenzymes such as GST pi or GST alpha can be performed as described in Example 3, herein.

Haloenol lactone inhibitors of GST isoenzymes can be further tested as described in Example 4 herein to determine the kinetic constants for inhibition of the GST isoenzyme. In addition, haloenol lactone compounds can be tested to determine if they are site specific, irreversible, mechanism-based inhibitors as described in Example 5, herein.

The haloenol lactone compounds of the invention can also be tested for their ability to overcome drug resistance to chemotherapeutic agents. For example, mammalian cell lines that have been made resistant to particular chemotherapeutic drugs can be used to identify haloenol lactone compounds that render the lines sensitive to the chemotherapeutic agents. Such cell lines are known to those of skill in the art and can be obtained for example from the American Type Culture Collection, Rockville, Md., USA.

In addition, the haloenol lactone compounds of the invention can be tested for their ability to overcome herbicide resistance by use of herbicide resistant plants, such as herbicide tolerant weeds.

F. Pharmaceutical Compositions and Methods

The haloenol lactones of the invention are useful for the prevention and treatment of drug resistance in cancer patients and for treatment of parasitic infections. The pharmaceutical compositions of the invention are suitable for use in a variety of drug delivery systems. Pharmaceutically acceptable carriers and formulations for use in the present invention are found in *Remington's Pharmaceutical Sciences,* Mack Publishing Company, Philadelphia, Pa., 17th ed. (1985), which is incorporated herein by reference. For a brief review of methods for drug delivery, see, Langer, *Science* 249:1527–1533 (1990), which is incorporated herein by reference.

The haloenol lactones of the present invention can be used in pharmaceutical compositions that are useful for administration to mammals, particularly humans. These compositions comprise the haloenol lactones of the invention and pharmaceutically acceptable carriers. These compositions are suitable for single administrations or a series of administrations.

The pharmaceutical compositions of the invention are intended for parenteral, topical, oral or local administration. For instance, the pharmaceutical compositions are administered parenterally, e.g., intravenously, subcutaneously, intradermally, or intramuscularly. A variety of pharmaceutically acceptable aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain as pharmaceutically acceptable carriers, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic pharmaceutically acceptable carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the haloenol lactones of the invention are preferably supplied in finely divided form along with a surfactant and propellant as pharmaceutically acceptable carriers. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides, may be employed. A carrier can also be included, as desired, as with, e.g., lecithin for intranasal delivery.

Pharmaceutical compositions containing the haloenol lactones of the invention are administered to a patient in order to prevent or reduce resistance to chemotherapeutic drugs, and thereby to potentiate the effects of chemotherapeutic drugs. The pharmaceutical compositions of the invention can be administered with the chemotherapeutic agents or separately. Amounts effective for this use will depend on, e.g., the particular haloenol lactone compound, the manner of administration, the weight and general state of health of the patient, and the judgment of the prescribing physician. Dosages, formulations and administration schedules may vary in cancer patients compared to normal individuals. In general, dosages range from about 0.1 to about 100 mg/kg body weight and more preferably from about 1 to about 50 mg/kg body weight. The patient's response can be measured, for example, by determining the effectiveness of the chemotherapy drugs. This is done, for example by assessing the clinical parameters for disease progression or regression. Measurements of GST enzyme activity from the patient's body fluids or tissue samples can also be useful in determining the dosage levels and for monitoring the patients response to the haloenol lactone.

The pharmaceutical compositions of the invention are also useful for the treatment or prevention of certain parasitic infections. Determination of the dosage for treatment of these infections is also subject to the variables described above. In general, dosages will range from about 0.1 to about 100 mg/kg body weight and more preferably from about 1 to about 50 mg/kg body weight. The patients' response can be measured, for example, by monitoring for the process of the parasitic infections.

H. Treatment of Plants to Prevent or Reduce Herbicide Resistance

The compounds of the invention are useful in preventing or reducing herbicide resistance in plants for a variety of herbicides, including chloracetanalides, thiocarbamates, and triazines such as atrazine.

The compounds of the invention can be applied alone or in a mixture with other plant regulators, fertilizers, pesticides herbicides, or fungicides. In particular, compounds of the invention can be applied along with a herbicide. The compositions may be applied in a mixture with a carrier or, if necessary, other auxiliary agents to form any one of the standard types of preparations commonly used in agriculture, for example, a dust, granules, grains, a wettable powder, an emulsion, an aqueous solution etc.

Suitable solid carriers are clay, talc, kaolin, bentonite, terra abla, calcium carbonate, diatomaceous earth, silica, synthetic calcium silicate kieselguhr, dolomite, powdered magnesia, Fuller's earth, gypsum and the like. Solid compositions may also be in the form of dispersible powders or grains, comprising, in addition to the active ingredient, a surfactant to facilitate the dispersion of the powder or grains in liquid.

Liquid compositions include solutions, dispersions or emulsions containing the active ingredient together with one or more surface-active agents such as wetting agents, dispersing agents, emulsifying agents, or suspending agents.

Surface-active agents may be of the cationic, anionic, or non-ionic type. Suitable agents of the cationic type include, for example, quaternary ammonium compounds. Suitable agents of the anionic type include, for example, soaps such as Triton® X-100 and Tween® 20; salts of aliphatic monoesters of sulphuric acid, for example sodium lauryl sulphate; and salts of sulphonated aromatic compounds, for example sodium dodecyl-benzenesulphonate, sodium, calcium, and ammonium lignosulphonate, butylnaphthalene sulphonate, and a mixture of the sodium salts of diisopropyl- and triisopropyl-naphthalene-sulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitanmonolaurate; the condensation product of the said partial esters with ethylene oxide; and the lecithins.

Suitable suspending agents are, for example, hydrophilic colloids, for example polyvinylpyrrolidone and sodium carboxymethylcellulose, and the vegetable gums, for example gum acacia and gum tragacanth. Preferred detergents are polyoxyethylenesorbitan (monolaurate) which is sold as Tween® 20 (Sigma Laboratories, St. Louis, Mo., USA), and α-[4-(1,1,3,3,-Tetramethylbutyl)phenyl]-ω-hydroxypoly(oxy-1,2-ethanediyl) where the number of ethoxy groups average 10, sold as Triton® X-100 (Rohm and Haas).

Aqueous solutions, dispersions or emulsions may be prepared by dissolving the active ingredient in water or an organic solvent which may, if desired, contain one or more wetting, dispersing, or emulsifying agents and then, in the case when organic solvents are used, adding the mixture so obtained to water which may, if desired, likewise contain one or more wetting, dispersing or emulsifying agents. Suitable organic solvents are ethylene dichloride, isopropylalcohol, propylene glycol, diacetone alcohol, toluene, mineral oil, kerosene, methylnapthalene, xylenes and trichloroethylene.

The active ingredients may also be formulated by microencapsulation. Microcapsules containing the desired tryptamine derivative may be prepared by co-acervation; or, more preferably, by stirred interfacial polymerisation of (for example) an isocyanate/diamine system. The resulting microcapsules may be used as an aqueous suspension.

The compositions which are to be used in the form of aqueous solutions, dispersions or emulsions are generally supplied in the form of a concentrate containing a high proportion of the active ingredient, and the concentrate is then diluted with water before use. These concentrates are usually required to withstand storage for prolonged periods and after such storage, to be capable of dilution with water in order to form aqueous preparations which remain homogeneous for a sufficient time to enable them to be applied by conventional spray equipment. In general, concentrates may conveniently contain from 10–60 percent by weight of the active ingredient or ingredients. Dilute preparations ready for use may contain varying amounts of the active ingredient or ingredients, depending upon the purpose for which they are to be used, and a dilute preparation containing between 0.01 and 10.0 percent and preferably 0.01 and 1 percent, by weight of active ingredient or ingredients may normally be used.

In carrying out the process of the invention, the amount of compound to be applied to prevent or reduce herbicide resistance in plants will depend upon a number of factors, for example the particular formulation selected for use, whether the compound is to be applied for foliage or root uptake, the herbicide that is used, and the identity of the plant species involved. However, in general, an application rate of from 0.01 to 100 kg per hectare is suitable, while an application rate of 0.1 to 10 kg per hectare is preferred for most purposes. In all cases routine tests can be used to determine the best rate of application of a specific formulation for any specific purpose for which it is suitable.

I. In vitro Diagnostic Methods

The haloenol lactone compounds of the invention are useful in the measurement of GST isoenzymes in diagnostic medicine. Preferentially, GST isoenzyme activity is measured in vitro. As described above, measurement of GST isoenzymes have a variety of uses in medicine. For example, measurement of GST pi isoenzymes in tissue specimens is useful for the detection or diagnosis of several different types of tumors, including lung cancers, colon cancers and breast cancers. In addition, measurement of GST alpha isoenzymes in body fluids is useful for the detection diagnosis or monitoring of a variety of disorders and conditions causing hepatocellular damage. These conditions and disorders include viral hepatitis, acute alcohol ingestion, and hepatic injury due to anesthesia or poisoning. See Beckett, et al., supra for a detailed description of the uses of GST isoenzyme measurements in medicine.

The haloenol lactone compounds of the invention can be used in GST enzyme assays to measure the activity of a particular isoenzyme. For instance, the haloenol lactone compounds of the invention preferentially selectively inhibit pi GST isoenzymes. GST enzyme activity attributable to GST pi isoenzyme can be measured by conducting standard GST enzyme assays in the presence and absence of a haloenol lactone that selectively inhibits the pi form of GST. Similarly, GST enzyme activity attributable to GST alpha isoenzyme can be measured by conducting a standard GST enzyme assay in the presence and absence of a haloenol lactone that selectively inhibits the alpha form of GST. GST enzyme assay methodology and protocols for determining the conditions under which an inhibitor selectively inhibits a particular GST isoenzyme are well known to those of skill in the art. (e.g., see Example 3, herein.)

EXAMPLES

Example 1: Synthesis of Methylidenetetrahydro-2-furanones

Methylidenetetrahydro-2-furanone derivatives 1 and 2 were synthesized by the reaction scheme shown in FIG. 1.

a) 2-Cinnamyl diethyl malonate synthesis:

Sodium metal (690 mg, 30 mg atom) was reacted with 20 ml of absolute ethanol at 0° C. After the sodium slices completely disappeared, diethyl malonate (4.5 ml, 30 mmol) was dropwise added at 0° C., followed by addition of 5.88 g (30 mmol) of cinnamyl bromide dissolved in 25 ml of absolute ethanol. The mixture was warmed to room temperature, stirred for 1.0 hr and filtered through a funnel with filter paper. The solvent was removed by rotary evaporation, the remains were redissolved in 100 ml of ethyl ether. The ether layer was washed with water (50 ml×3) and dehydrated with anhydrous $Na_2SO_4$, followed by rotary evaporation. 2-Cinnamyl diethyl malonate was isolated by flash chromatography over silica gel eluted with 20% $CHCl_3$. The product was characterized by NMR spectroscopy. $^1$H NMR (300 MHz, $CDCl_3$): δ ppm 1.25 (t, J=7.1 Hz, 6H), 2.77–2.82 (m, 2H), 3.48 (t, J=7.6 Hz, 1 H), 4.20 (q, J=7.1 Hz, 4H), 6.18 (tt, J=7.1, 15.8 Hz, 1H), 6.48 (d, J=15.8 Hz, 1H), 7.20–7.34 (m, 5H).

b) 2-Cinnamyl-4-pentynoic acid synthesis:

A NaOEt/EtOH solution was prepared by reacting 167 mg of sodium metal (7.3 mg atom) with 20 ml of absolute ethanol. 2-Cinnamyl diethyl malonate (1.33 g, 4.8 mmol) was slowly added to the NaOEt/EtOH solution, followed by dropwise addition of 0.8 ml of propargyl bromide (80% wt. solution in toluene, 7.2 mmol) in 10 ml of absolute ethanol. The mixture was stirred at room temperature overnight and mixed with 20 ml of 2N NaOH solution. The mixture was heated with stirring at 80° C. for 2 hr, and the ethanol was removed by rotary evaporation. The aqueous layer was washed with ethyl acetate (10 ml×2) and acidified with 6N HCl to pH 1–2. The acidified solution was extracted with ethyl acetate (20 ml×3), and the extracts were dried over $Na_2SO_4$ and evaporated in vacuo to remove solvent. The resulting yellowish oil was heated under vacuum in an oil bath at 135° C. for 3 hr and loaded onto a silica gel column. 2-Cinnamyl-4-pentynoic acid was purified through the flash chromatography eluted with 20% ethyl acetate in hexane in the presence of 0.1% trifluoroacetic acid. The product was characterized by NMR spectroscopy. $^1$H NMR (300 MHz, $CDCl_3$): δ ppm 2.03 (s, 1H), 2.45–2.79 (m. 5H), 6.14 (tt, J=7.2, 15.7 Hz, 1 H), 6.49 (d, J=15.7 HZ 1 H), 7.18–7.36 (m, 5H).

c) 3-Cinnamyl-5(E)-bromomethylidenetetrahydro-2-furanone (Compound 2) synthesis:

3-Cinnamyl-4-pentynoic acid (188 mg, 0.88 mmol) was dissolved in 10 ml of $CH_2Cl_2$, followed by sequential addition of 88 mg of $KHCO_3$ (0.88 mmol), 175 μl of $BU_3NOH$ (40% in $H_2O$) and 158 mg of N-bromosuccinimide (0.88 mmol). After vigorous stirring at room temperature for 30 min, the mixture was diluted with 10 ml of $CH_2Cl_2$ and washed with 5% $Na_2S_2O_3$, brine and water (10 ml×2 each step). The $CH_2Cl_2$ layer was dried by anhydrous $Na_2SO_4$, and the organic solvent was removed by rotary evaporation. The chromatography of the crude product over silica gel eluted with 10% ethyl acetate in hexane afforded 47 mg of colorless oil. The product was characterized by NMR spectroscopy. TLC: Silicagel 60 $F_{254}$ (Merck), ethyl acetate/hexane (50/50), $R_F$=0.68. $^1$H NMR (300 MHz, $CDCl_3$): δ ppm 2.50–2.81 (m, 3H), 2.96–3.14 (m, 2H), 5.98 (t, J=2.1 Hz, 1H), 6.11 (tt, J=7.2, 15.6 Hz, 1H), 6.52 (d, J 15.9 Hz, 1H), 7.19–7.37 (m, 5H). The structure of compound 2 is shown in FIG. 1.

d) 3-Cinnamyl-(α,β-epoxy)-5(E)-bromomethylidenetetrahydro-2-furanone (compound 1) synthesis:

A solution containing 3-cinnamyl-5(E)-bromomethylidenetetrahydro-2-furanone, compound 2, (24 mg, 0.082 mmol) in 1.0 ml of $CHCl_3$ was cooled in an ice bath for 10 min. To the solution was slowly added 42 mg of m-chloroperoxybenzoic acid (50% in purity, 0.123 mmol) dissolved in 1.0. ml of $CHCl_3$. The mixture was stirred at room temperature for 12 hr and washed with saturated $NaHCO_3$ solution then $H_2O$ (1.0 ml×3 each step). After dehydration by anhydrous $Na_2SO_4$, the $CHCl_3$ layer was concentrated by evaporation in vacuo and loaded on a preparative TLC plate (Silicagel 60 $F_{254S}$, 2 mm thick, Merck), and the TLC plate was developed with 70% $CHCl_3$ in hexane. The TLC purification afforded 9.0 mg of colorless oil. The product was characterized by NMR spectroscopy. TLC: Silicagel 60 $F_{254}$ (Merck), chloroform/hexane (75/20), $R_F$=0.26. $^1$H NMR (300 MHz, $CDCl_3$): δ ppm 1.76–2.44 (m, 2H), 2.70–2.80 (m, 1H), 3.02–3.16 (m, 2H), 3.21–3.32 (m, 1H), 3.69 (d, J=11.1 Hz, 1H), 6.00 (s, 1H), 7.25–7.38 (m, 5H). The structure of compound 1 is shown in FIG. 1.

Example 2: Purification of Glutathione S-transferase Isozymes

The three major mouse liver GST isoenzymes were purified according to established methods. Male CD-1 mice, 25–35 g, were purchased from Charles River Breeding Laboratories, Inc. (Wilmington, Mass.). Animals were housed on autoclaved pine shavings in approved animal care facilities and fed ad libitum for 1 week prior to cervical dislocation.

Mice were killed by cervical dislocation and livers were removed, rinsed with ice-cold 10 mM Tris buffer (pH 7.4) containing 0.25 M sucrose, 1 mM EDTA and 1 mM DTT (buffer A). The tissues were homogenized in buffer A (1 g tissue/2 mL buffer). Centrifugation and all subsequent purification steps were carried out at 4° C. The homogenate was centrifuged at 10,000 g for 30 min. The supernatant fraction was then collected and centrifuged at 100,000 g for 80 min. Supernatant was next passed through a Sephadex G-25 Column (100 cm×2.5 cm) which had been pre-equilibrated in 25 mM potassium phosphate buffer (pH 7.4) containing 1 mM EDTA and 1 mM DTT (buffer B). Column eluants were monitored at 280 nm using an Isco-UA5 detector. The elutant from the G-25 column containing GST activity was applied to an affinity column (11 cm×2.5 cm, GSH-linked agarose, Sigma) at a flow rate of 0.64 ml/min. The first two GST isozymes were eluted using a linear gradient (0–75 mM) of GSH in buffer b (250 mL×250 mL). The third peak containing activity towards CDNB was eluted by using a linear gradient of increasing pH (7.4–9.0) in buffer b which was 75 mM in GSH (150 mL×150 mL). The three main peaks of activity were recovered and pooled separately. Each pool was concentrated to 25–30 mL in an Amicon ultrafiltration cell (Amicon, Inc., Beverly, Mass., USA) with a PM 10 membrane and dialyzed against 4L nanopure water. Pooled proteins were analyzed by ESI/MS to determine purity and subunit molecular weight. Dialyzed concentrates were lyophilized and stored at −80° C.

Example 3: Selective Inhibition of GST Isoenzymes by Compounds 1 and 2

The selective inhibition of GST pi isoenzymes by compounds 1 and 2 was demonstrated as described below. Compounds 1 and 2 were synthesized and purified and described in Example 1, and GST isoenzymes alpha, mu, and pi were isolated from mouse liver as described in Example 2.

For the enzyme inhibition studies, solutions of alpha, mu and pi glutathione S-transferase (1.0 µg/µl) were prepared in a 0.1 M potassium phosphate buffer (pH 6.5). To 350 µl of 0° C., 0.1 M potassium phosphate buffer (pH 6.5) was sequentially added 10 µl of the reconstituted GST solution and 5 µl of an ethanol solution containing compound 1 or compound 2. The mixture (50 µl) was aliquated for enzyme activity assay and immediately incubated in a water bath at 37° C. Aliquots were withdrawn at 1, 3, 5, 8 and 12 min, and GST activity was measured using GSH and CDNB as substrates according to the method of Habig et al. (1974) *J. Biol. Chem.* 249:7130–7139.

In brief, the activity of the enzyme was determined in a 0.1 M potassium phosphate buffer (pH 6.5) containing 1 mM GSH and 1 mM CDNB using an extinction coefficient of 9.6 $mM^{-1}$ $cm^{-1}$. One unit of enzyme is defined as the amount required to catalyze the conjugation of 1 µmol of substrate to GSH per min at 25° C. The rate of product formation was monitored by measuring the change in absorbance at 340 nm using a Shimadzu PC-2101 uv-visible spectrophotometer (Shimadzu Scientific Instruments, Columbia, Md., USA). Specific activities are based on protein concentrations as determined by the Bradford protein determination kit from Biorad, Hercules, Calif., USA, using bovine serum albumin as a reference.

Figure 3:
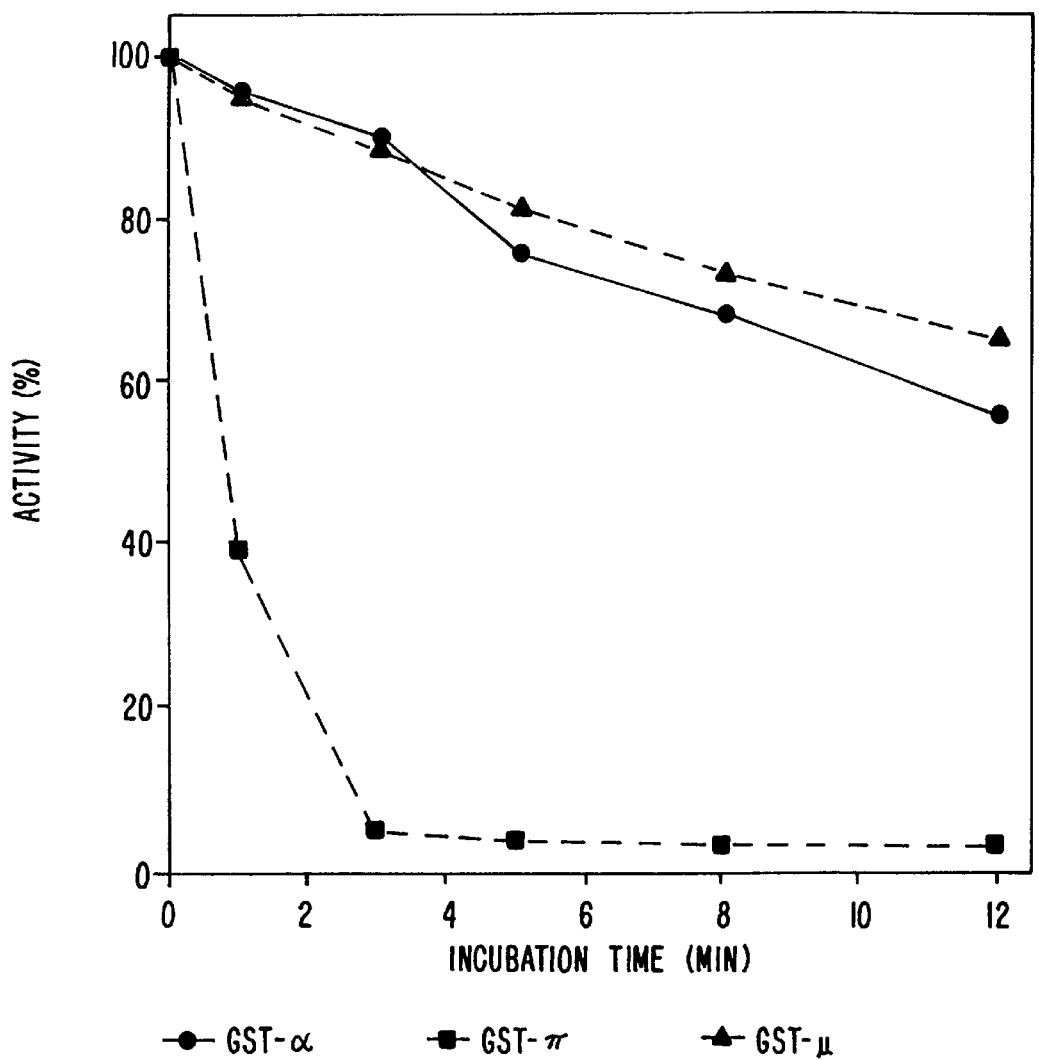
FIG. 3: Inactivation of glutathione S-transferase (GST) isozymes by haloenol lactone compound 1. The GST concentration was 1.0. μM, and haloenol lactone 1 concentration was 100 μM. ●, GST-α; ■, GST-π, ▲, GST-μ.
Figure 4:
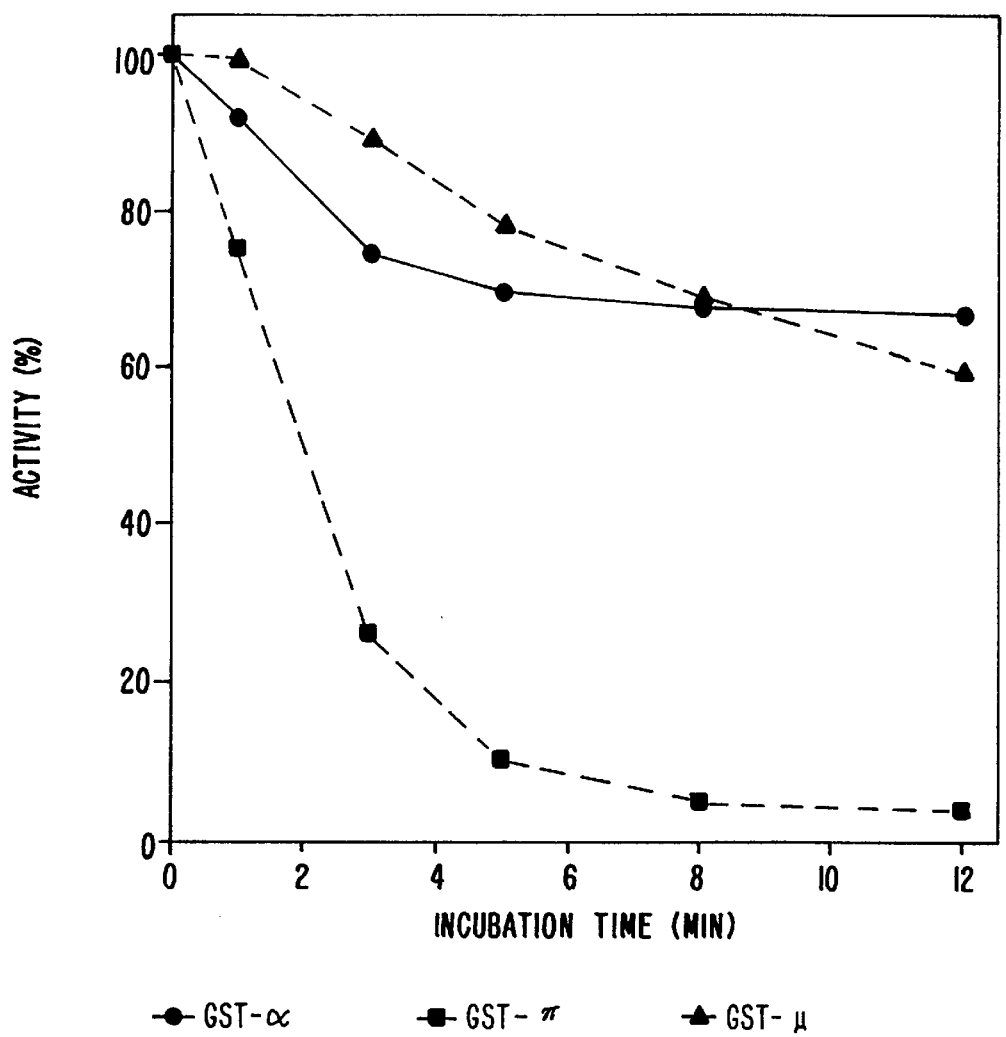
FIG. 4: Inactivation of glutathione S-transferase (GST) isozymes by haloenol lactone compound 2. The GST concentration was 1.0 μM, and haloenol lactone 2 concentration was 100 μM. ●, GST-α; ■, GST-π, ▲, GST-μ.

The inhibition of the GST isoenzyme fractions alpha, mu and pi was determined at 5 different time points as described above. As shown in FIG. 2, the GST pi isoenzyme was selectively inhibited by compound 1. After 5 minutes, the enzyme activity of GST pi was completely inhibited by a 100 µM concentration of compound 1, whereas about 80% of the enzyme activity GST alpha and mu remained. (See FIG. 3.) Similar results for the inhibition of the GST isoenzymes by compound 2 is shown in FIG. 3. After five minutes incubation with a 100 µM concentration of compound 2, the enzymatic activity of GST pi was completely inhibited. In contrast, from 70% to 80% of the enzyme activity of GST alpha and GST mu remained under the same conditions (see FIG. 4).

Example 4: Determination of Kinetic Constants for Inhibition of GST Pi Isoenzyme by Compounds 1 and 2

Kinetic constants for the inhibition of GST pi isoenzyme by compounds 1 and 2 were determined as described below. Compounds 1 and 2 were synthesized and purified as described in Example 1, and GST pi isoenzyme was isolated from mouse liver as described in Example 2. Enzyme inhibition studies were performed as described in Example 3, except that four different concentrations of inhibitor were used. Enzyme assays were performed as described in Example 3.

Figure 5:
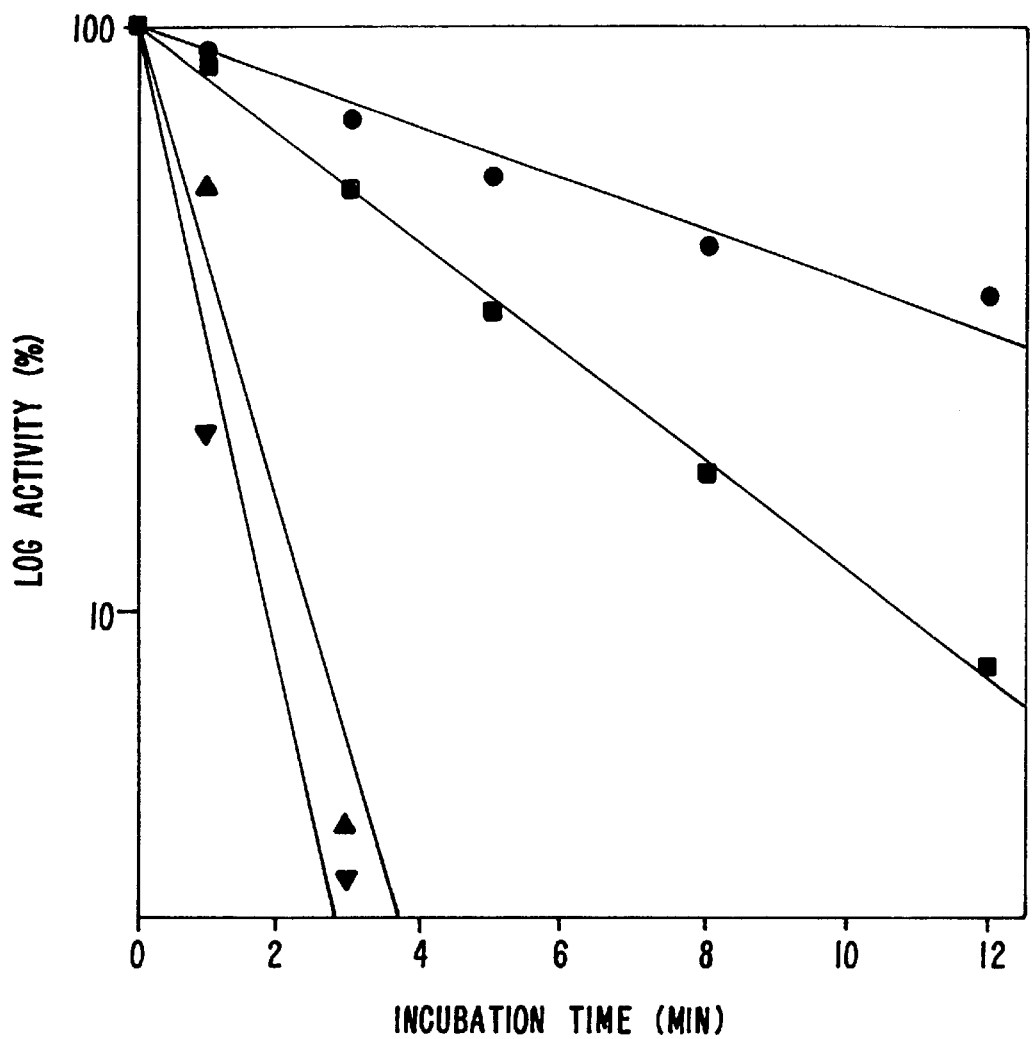
FIG. 5: Inactivation of glutathione S-transferase (GST) pi isozyme by haloenol lactone/epoxide. GST pi (1.0 μM) was incubated at 37° C. with haloenol lactone compound 1 at a concentration of 6.85 μM, ●; 13.7 μM, ■; 68.5 μM, ▲; 137 μM, ▼. Aliquots were withdrawn, and the GST activity was determined periodically as shown.
Figure 6:
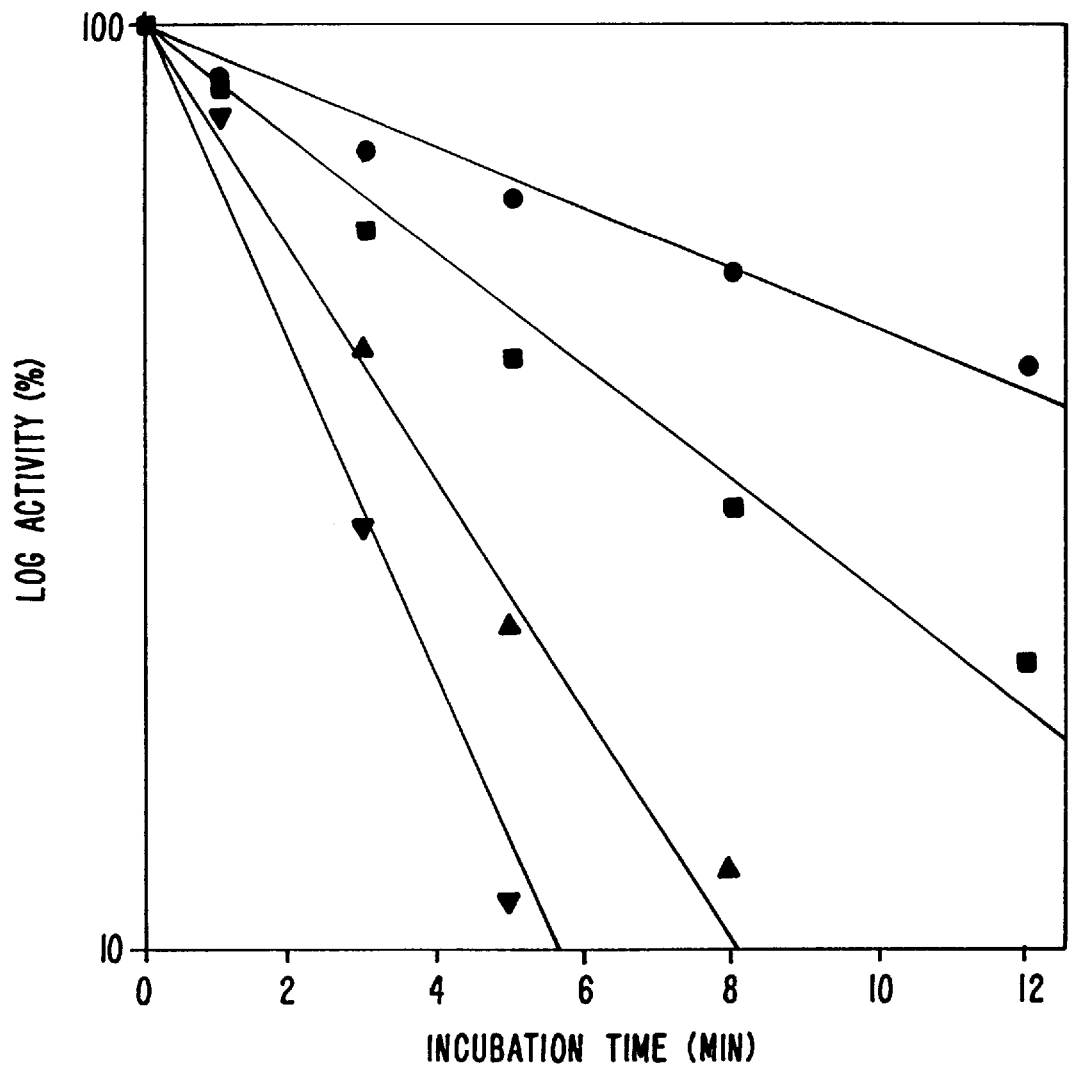
FIG. 6: Inactivation of glutathione S-transferase (GST) pi isozyme by haloenol lactone/alkene. GST pi (1.0 μM) was incubated at 37° C. with haloenol lactone compound 2 at a concentration of 13.7 μM, ●; 34.3 μM, ■; 68.5 μM, ▲; 137 μM, ▼. Aliquots were withdrawn, and the GST activity was determined periodically as shown.

The kinetics of inhibition of GST pi isoenzyme at four different concentrations of compound 1 or compound 2 is shown in FIGS. 5 and 6, respectively. $k_{inact}$ and $K_I$ constants were calculated from this data as described by Jung, et al. (1975) *Biochem. Biophys. Res. Comm.* 67:301–306. $k_{inact}$=1.19 $min^{-1}$ and $K_I$=64.43 µM were calculated for the inhibition of GST pi isoenzyme by compound 1. This yielded a $k_{inact}/K_I$ ratio of 18.47×$10^3$ $min^{-1}$×$M^{-1}$. $k_{inact}$=0.56 $min^{-1}$ and $K_I$=86.70 µM were calculated for the inhibition of GST pi isoenzyme by compound 2. This yielded a $k_{inact}/K_I$ ratio of 6.46×$10^3$ $min^{-1}$×$M^{-1}$.

Example 5: Irreversible Inhibition and Covalent Modification of GST Pi Isoenzyme by Compound 2

The irreversible inhibition of and covalent modification of GST pi isoenzyme by compound 2 was demonstrated as described below. Compound 2 was synthesized and purified as described in Example 1, and GST pi isoenzyme was isolated from mouse liver as described in example 2.

Figure 7:
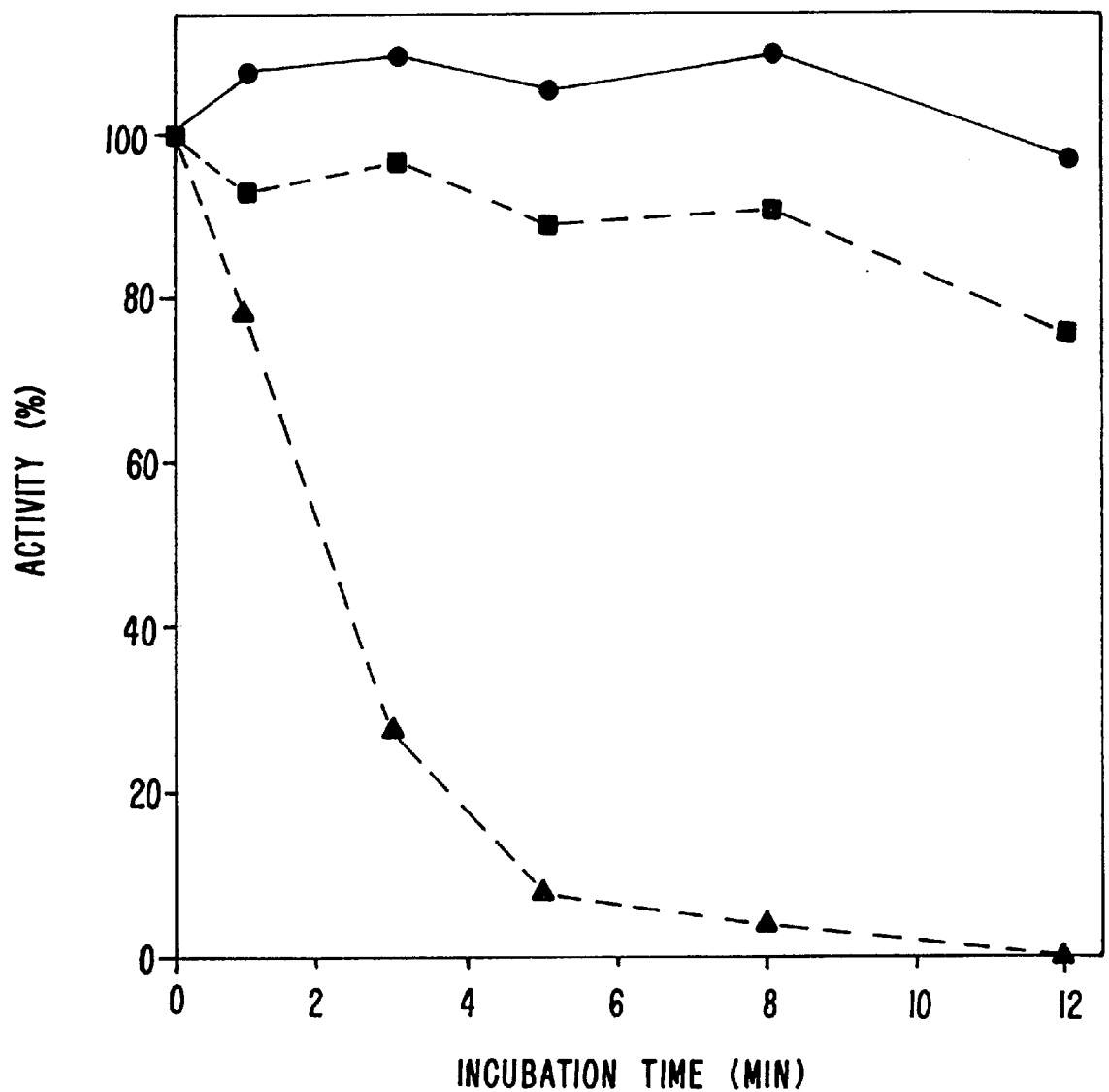
FIG. 7: Inactivation of glutathione S-transferase (GST) pi isozyme by haloenol lactone 2. The GST concentration was 1.0 μM): ●, control; ▲, +haloenol lactone 2 (200 μM), no S-hexylglutathione; ■, +haloenol lactone 2 (200 μM), +S-hexylglutathione (2,000 μM).

The time-dependent inhibitory effect of compound 2 on GST was shown to be inhibited by S-hexylglutathione. Enzyme inhibition studies and enzyme assays for this experiment were performed as described in Example 3. S-hexylglutathione dissolved in a 0.1 M potassium phosphate buffer (pH 6.5) was added in the incubation solution. Time-dependent inhibition for GST by compound 2 was observed, and the enzyme was totally inactivated in 8 minutes with a $t_{1/2}$ of less than 3 min. In this experiment, we incubated compound 2 with GST-pi isozyme in the presence of S-hexylglutathione (2,000 µM), a competitive inhibitor of GST. As expected, S-hexylglutathione completely suppressed the time-dependent inhibition of GST by compound 2. (See FIG. 7).

In order to confirm the irreversible enzyme inhibition, a 10-fold excess of compound 2 was incubated with the pi isozyme at 37° C. for 3 hours, followed by dialysis against 6 changes of Nanopure water. The dialyzed protein sample was dried by lyophilization. The recovered protein was re-dissolved in water, and specific enzyme activity was determined by measuring the protein content and GST activity. The activity of GST modified by compound 2 was not restored by exhaustive dialysis, and only 7.8% of enzyme activity for the modified GST remained relative to the control. This finding indicated that GST was irreversibly inhibited and covalently modified by compound 2.

To further confirm the covalent modification of GST, both native and modified enzymes were analyzed using electrospray ionization mass spectrometry (ESI/MS). The procedure for mass spectroscopy was as follows. Lyophilized proteins were dissolved in 50/50 ACN/water to give a final concentration of 1 µg/µl (40 pmol/µl). Intact proteins were analyzed on a VG/Fisons Quattro-BQ triple quadrupole mass spectrometer (VG Biotech, Altrincham, UK) using 50/50 ACN/water+1% formic acid as the mobile phase. An Isco µLC-500 syringe pump delivered the mobile phase at 5 µL/min. Proteins were analyzed by direct flow injection using an injection volume of 10 µL. Spectra were obtained in positive ion mode using a capillary voltage of +3.5 KV, and the source temperature was held at 65° C. The cone voltage was set between 35 and 50 V. Spectra were scanned over the range of 600–1400 Da/e at 10 s/scan and summed using the MCA acquisition mode in the Fisons Masslynx software.

Figure 8A:
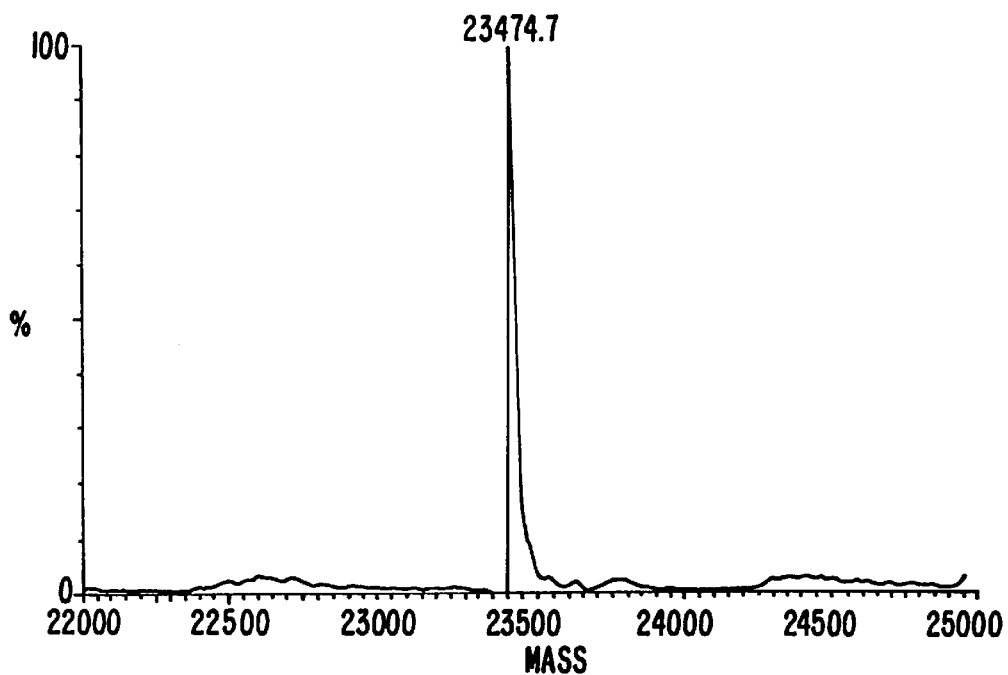
FIG. 8: Electrospray ionization MaxEnt™ transformed mass spectra of native GST pi isozyme (top) and modified GST-pi isozyme (bottom). GST pi isozyme was incubated with vehicle or a 10-fold excess of lactone 1 at 37° C. for 3 hr, followed by 6 changes of dialysis against Nanopure water at 4° C.
Figure 8B:
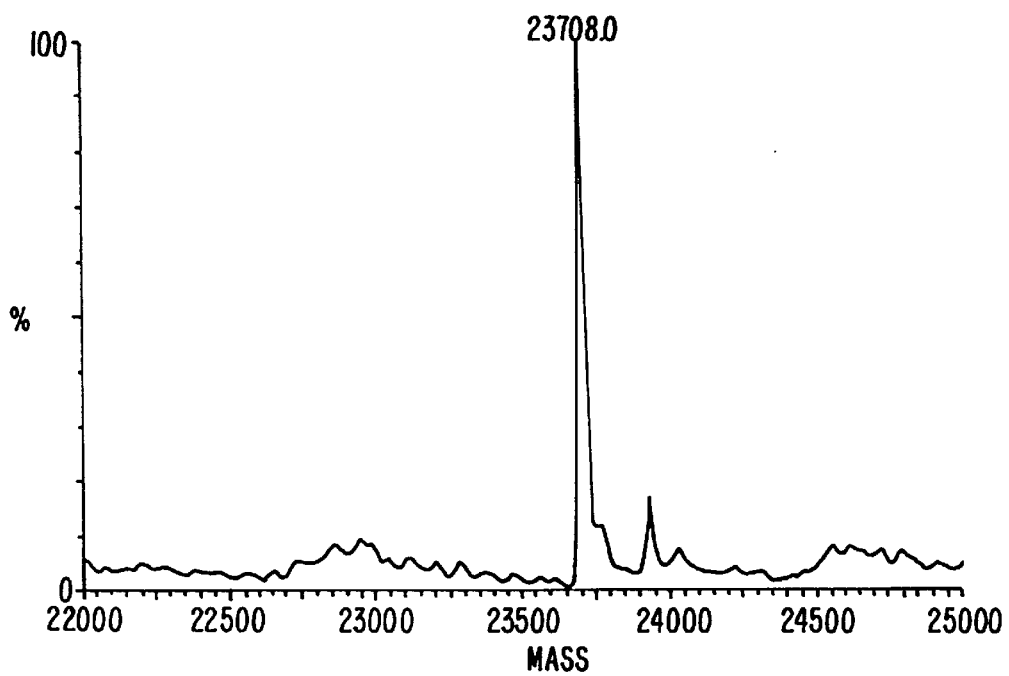
Figure 9:
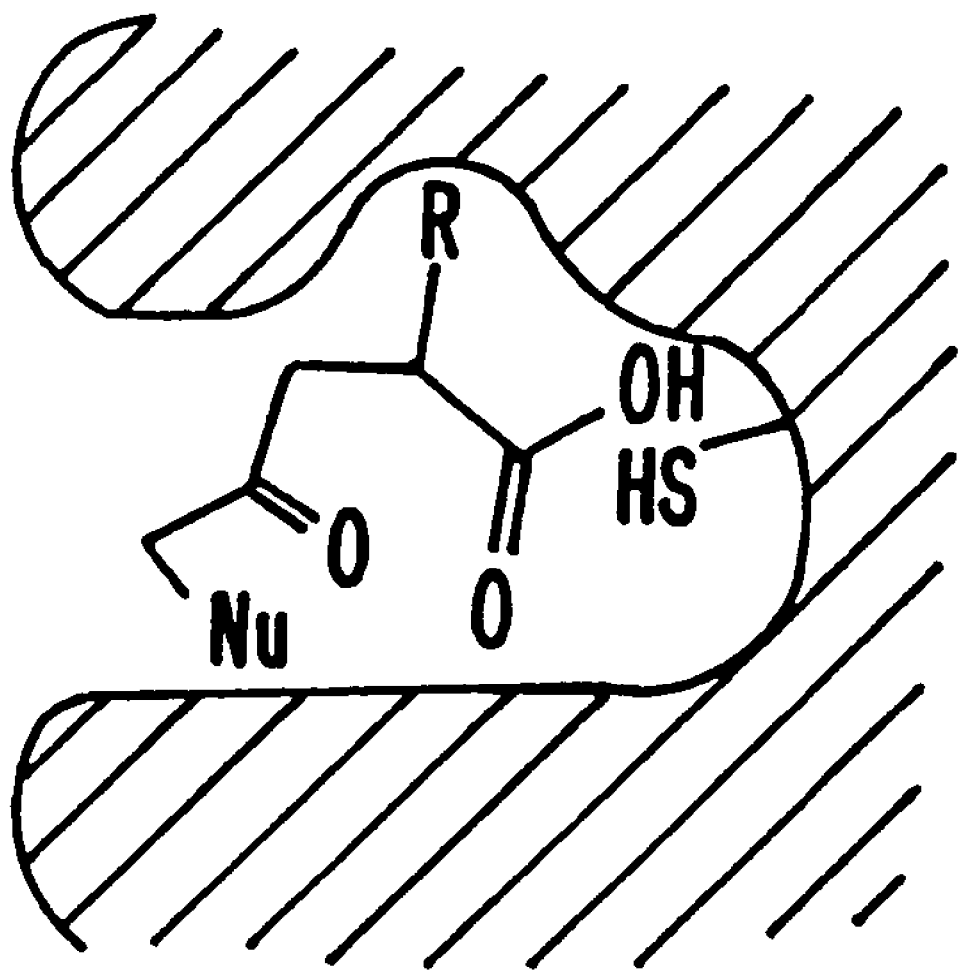
FIG. 9: Proposed structure of adduct of compound 2 with GST pi observed by electrospray mass spectroscopy.

As expected, no native GST (23,479 Da) was observed in the ESI mass spectrum of modified GST (see FIG. 8). Interestingly, a mass addition of 230 Da rather than 212 Da (the molecular weight of adduct 2 of FIG. 8, see below) relative to the molecular weight of native GST pi isozyme was observed after incubation with inhibitor. This mass addition matched the molecular weight of GST inhibitor adduct 3 shown in FIG. 9, which is the hydrolyzed protein product of adduct 2 (see FIG. 10). It is unknown whether the hydrolysis of adduct 2 occurred during the process of inactivation or during the dialysis. However, these mass spectrometric results indicated a loss of bromine from compound 2 and demonstrated strong evidence for the second nucleophilic attack by a nucleophile of the enzyme at the Cα, linked with a bromine (See FIG. 10). The mass spectroscopy data combined with finding that S-hexylglutathione blocks the inhibition of GST by compound 2 indicates that compound 2 inhibits the enzyme by chemical modification at the active site rather than random modification at other sites.

Figure 10:
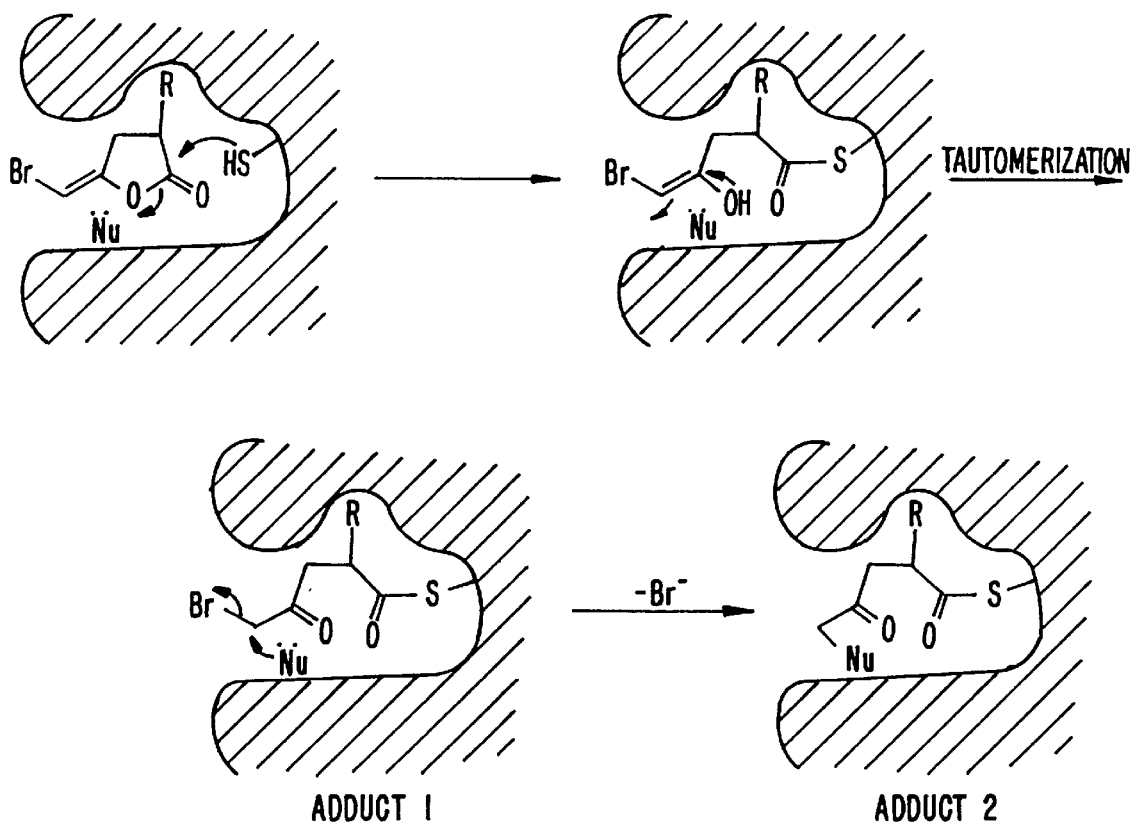
FIG. 10: Proposed scheme of mechanism based inhibition of GST pi isoenzyme by compound 2.

As described above, we rationally designed and synthesized a haloenol lactone derivative, compound 2, as a mechanism-based inactivator of GST. While not wishing to be bound by theory, three consecutive steps of active site-directed chemical reactions shown in FIG. 10 are proposed as the mechanism of enzyme inactivation. In this mechanism, a sulfhydryl group in the GST active site initiates protein modification by opening the haloenol lactone ring, followed by tautomerization of the haloenol (anion) to the α-halo keto form (adduct 1 in FIG. 10). According to this mechanism, the resulting α-bromo ketone reacts further with a nucleophilic amino acid residue at the active site, covalently modifying and inactivating the enzyme (adduct 2 in FIG. 10).

In summary, we have discovered compounds 1 and 2 as mechanism-based inactivators of glutathione S-transferase. These compounds showed a time-dependent and irreversible inhibitory effect on GST pi isozyme. The bromine of the haloenol lactone is lost during the inactivation of GST, and the chemical modification takes place at the active site of the enzyme. While not wishing to be bound by theory, the process of the enzyme inactivation may involve two consecutive steps of nucleophilic attack on the electrophilic centers of these compounds. The discovery of this mechanism-based inactivator of GST also allows us to further study the catalytic mechanism of GST, in addition to the uses described herein.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for detecting a glutathione-S-transferase isoenzyme in a biological specimen comprising the measurement of glutathione-S-transferase enzymatic activity in the presence and absence an amount of a compound of the formula:

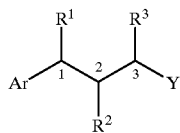

in which:

Ar is an aryl group;

$R^1$ and $R^2$:

a) together form a double bond between carbon atoms 1 and 2;

b) together form an epoxy group between carbon atoms 1 and 2: or c) are the same or different and are independently selected from the group consisting of H, OH, glutathione thioether, glutathione-S-oxide thioether, and glutathione-S,S-dioxide thioether;

$R^3$ is selected from the group consisting of H, OH, glutathione thioether, glutathione-S-oxide thioether, and glutathione-S,S-dioxide thioether; and Y is a haloenol lactone, wherein said amount is effective to selectively inhibit said glutathione-S-transferase isoenzyme.

2. The method of claim 1 wherein Ar is a radical of the formula:

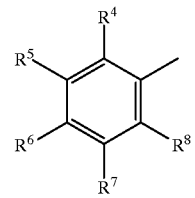

in which:

$R^4$, $R^5$, $R^6$, $R^7$, and $R^8$ are the same or different and are independently selected from the group consisting of H, a $C_1$–$C_5$ alkyl group, a $C_1$–$C_5$ alkoxy group, a halogen, $NO_2$, and $CF_3$.

3. The method of claim 2 wherein Y is a radical of the formula:

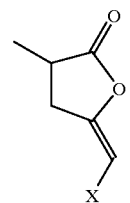

wherein X is halogen.

4. The method of claim 3 wherein $R^4$–$R^8$ are H; $R^1$ and $R^2$ together form a double bond between carbon atoms 1 and 2; and $R^3$ is H.

5. The method of claim 3 wherein $R^4$–$R^8$ are H; $R^1$ and $R^2$ together form an epoxy group between carbon atoms 1 and 2; and $R^3$ is H.

6. The method of claim 1 wherein said glutathione-S-transferase isoenzyme is a pi isoenzyme.

* * * * *